United States Patent [19]

Sato

[11] Patent Number: 4,468,465

[45] Date of Patent: Aug. 28, 1984

[54] DIAGNOSING CANCER BY OBSERVING MARKER GLYCOSAMINOGLYCANS EXTRACTED FROM PATIENT

[76] Inventor: Clifford S. Sato, 11018 Bellbrook Dr., Houston, Tex. 77096

[21] Appl. No.: 415,774

[22] Filed: Sep. 7, 1982

[51] Int. Cl.$^3$ ............... G01N 33/50; G01N 27/26
[52] U.S. Cl. ................................ 436/64; 204/403; 436/63; 436/94; 536/55.1
[58] Field of Search ................. 436/94, 63, 64; 536/55.1; 204/403

[56] References Cited

U.S. PATENT DOCUMENTS 4,115,062 9/1978 Morre ............................ 436/64
4,389,392 6/1983 Adachi ........................ 436/64 X

OTHER PUBLICATIONS

J. D. Ford et al., Anal. Biochem., 84, 539–550 (1978).
K. Pietila et al., Anal. Biochem., 116, 317–318 (1981).
E. H. Schuchman, Anal. Biochem., 117, 419–426 (1981).

Primary Examiner—Sidney Marantz
Attorney, Agent, or Firm—Bill B. Berryhill

[57] ABSTRACT

A disease-specific marker for cancer and hyperplasia of the human prostate comprising hybrid and copolymer glycosaminoglycans (GAGs) extracted from the patient and methods for diagnosing and monitoring treatment of cancer and hyperplasia of the prostate by observing such hybrid and copolymer GAGs.

5 Claims, 2 Drawing Figures

DIAGNOSING CANCER BY OBSERVING MARKER GLYCOSAMINOGLYCANS EXTRACTED FROM PATIENT

BACKGROUND OF THE INVENTION

1. Field of the Invention

The present invention pertains to disease-specific markers for cancer and hyperplasia of the human prostate. Specifically, the present invention pertains to disease-specific markers suitable for diagnosing and monitoring the treatment of cancer and hyperplasia of the human prostate.

2. Brief Description of the Prior Art

The two major diseases of the human prostate are cancer and hyperplasia. While some investigators theorize that hyperplasia is an early state of cancer activity, others feel that it is a totally unrelated disease. The incidence of both cancer and hyperplasia of the prostate accelerate after the age of fifty. In the United States, in men past the age of fifty, the age gradient for cancer of the prostate is steeper than that of any other cancer site, and prostate cancer is the foremost killer of men seventy years of age and older. While seemingly related to aging the actual molecular mechanisms of the cause and devastating growth of cancer are not yet understood.

Computed tomography scanning, ultrasound, aspiration techniques and definitive pelvic lymph node disections have contributed toward assessment of the extent of prostate cancer. However, the use of these methods in diagnosing, treating and understanding prostatic cancer are dubious.

In the past two decades, isolation and measurement of prostatic specific acid phosphatase has been proposed as a means for diagnosing and monitoring the treatment of prostatic cancer. Several tests utilizing radioimmunoassay, counterimmune electrophoresis, etc., have been utilized to detect circulating acid phosphatase of prostatic origin. While initially accepted with great enthusiasm, it has become apparent that wide variations of results exist with these methods. Consensus is emerging that use of such methods for detection of unsuspected cancer of the prostate in the general population would not be feasible due to the large number of falsely positive results.

Changes in normal serum glycoprotein levels have long been associated with malignancy. Recent investigations have confirmed that changes in specific glycoprotein do indicate cancer activity. See "Preparation and Properties of Glycoprotein Associated with Malignancy", Bolmer, Sally Delong, and Davidson, Eugene A., (1981), Biochemistry 20: 1047. However, changes in glycoprotein levels are not specific to prostate cancer.

Very recent investigation of serum prostate-specific antigen (PA) and prostatic acid phosphatase (PAP) indicate that a multiple marker test of tissue specific antigens may be of additive value in the immunodiagnosis of cancer. See "Multiple Marker Evaluation in Human Prostate Cancer with the Use of Tissue Specific Antigens", Kuriyama, M.; Wang, M. C.; Lee, C. L.; Killian, C. S.,; Papsidero, L. D.; Inaji, H.; Loor, R. M.; Lin, M. F.; Nishiura, T.; Slack, N. H.; Murphy, G. P. and Chu, T. M., JNCI 1982; 68:99. The same investigation refers to the present unavailability of human tumor-specific markers for prostate cancer.

A marker-molecule that is specific for cancer could offer impetus toward the understanding of the biochemical process involved in cancer. A good marker-molecule would identify the disease and would act as a guide for the various stages of cancer. It would be good for diagnostic, prognostic, and treatment purposes. Unfortunately, as already pointed out, cancer specific marker molecules of the prostate have been elusive and difficult to discover.

SUMMARY OF THE INVENTION

The present invention is the discovery of a disease specific marker for cancer and hyperplasia of the human prostate comprising glycosaminoglycans (GAGs) extracted from the host or patient. It is proposed that these glycosaminoglycans (GAGs) be used in diagnosing and monitoring the treatment of cancer.

It is proposed that the presence of cancer and hyperplasia of the human prostate be diagnosed by observing glycosaminoglycans (GAGs) extracted from the patient and that treatment of prostatic cancer and hyperplasia be monitored by observing the response of glycosaminoglycans (GAGs) to certain tests. Since this is the first disease-specific marker found for cancer and hyperplasia of the human prostate, the importance thereof is obvious. The apparent objects and advantages of the invention will be more clearly understood from reading the specification which following in conjunction with the accompanying drawings.

DESCRIPTION OF PREFERRED EMBODIMENTS

Figure 1:
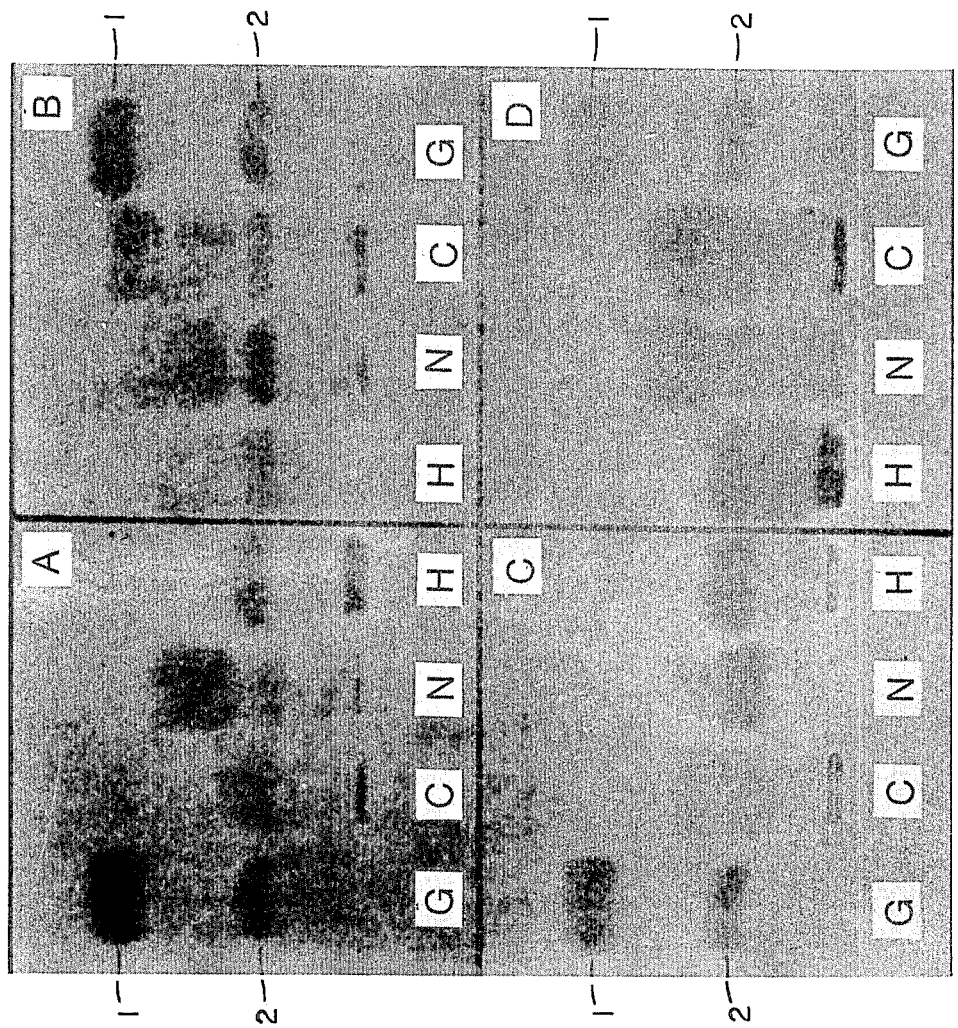
FIG. 1 represents an electropherogram of glycosaminoglycans (GAGs) extracted from cancerous, normal and hyperplastic human prostates demonstrating unique GAG patterns.

In an attempt to discover cancer specific marker molecules, zinc was selected as a possible lead because of two well established findings: (1) the zinc content of the normal human prostate is higher than that of any other organ in the body; and (2) this relatively high zinc content decreases to less than one-third in cancer but increases by almost two and one-half fold in hyperplasia. Prostate zinc thus appears to have some value as a marker. However, since zinc appears in many parts of the body, it is not a disease-specific marker.

For further investigation, the question was asked: "Is prostate zinc bound to tissue structure or free to move about?" If zinc is tissue-bound then it might be considered as a "secondary" marker and the zinc binding macromolecule to be the "primary" marker. On the other hand, if prostate zinc is not tissue-bound, but free, this distinction might not be made.

To determine whether prostate zinc is bound or free, one approach is to first determine whether prostate tissues are capable of binding zinc. To make this determination, thin sections of formalin-fixed human prostates are placed in ice-cold solutions of radioactive zinc. After ten minutes, the tissue sections are thoroughly washed with cold water and the radioactivity measured. Experiments demonstrate that prostate tissues do bind zinc and that bound zinc is not removed by washing with cold water.

To determine what structural macromolecule is responsible for binding zinc, additional tests may be made. It is presupposed that protein could bind zinc by means of chelation and that acidic polysaccharides could bind zinc by means of ionic charges. After experimentation, protein may be ruled out as the major zinc binder. This may be done by binding tissue sections with radioactive zinc. After thoroughly washing with cold water, the tissue sections are rinsed in dilute acetic acid. The acid rinse effectively removes all the radioactive zinc. Since an ionic bond of zinc salt is generally weaker than a zinc chelate, it is assumed that positively charged zinc ions were bound to acid polysaccharides having carboxyl or ester sulfate or both groups. If the negative charges of the carboxyl and ester sulfate groups are responsible for binding zinc in the tissue sections, removal of these negative charges should prevent the binding of zinc by the tissues. This concept may be tested, after the effective removal of negative charges of carboxyl and ester sulfate groups, by treating the tissues with a dilute solution of hydrogen chloride in methanol. By this treatment, the carboxyl group is methoxylated and the ester sulfate cleaved. When tissues so treated are then permitted to bind zinc, the amounts of zinc bound is only two percent to five percent of the amounts bound by the untreated tissues. The two percent to five percent of bound zinc could represent protein-bound zinc.

From such tests, it thus appears clear that the macromolecule responsible for binding most of the prostate zinc is an acid polysaccharide. The family of acid polysaccharides possessing carboxyl and ester sulfate groups could be glycosaminoglycan, hereinafter referred to as G-A-G or GAG. Seven different classical species of GAGs are recognized: chondroitin 4-sulfate; chondroitin 6-sulfate;; dermatan sulfate, hyaluronate; heparin; heparan sulfate and keratan sulfate. Of the seven species of GAGs, keratan sulfate and heparin have not been detectable in either the mouse or human prostate.

In earlier reports, GAGs were considered to be simple, linear polymers made up of repeating disaccharide units, except for heparan sulfate and heparin, which were considered to be made up of repeating tetra- or hexasaccharide units. Presently, there is a greater awareness of heterogeneity in the molecular structure of GAGs. As an illustration, there are differences in the degree of sulfation and also differences in the distribution of sulfate along a molecule. There are hybrids or copolymers, made up of various lengths of fragments of two or more species. Moreover, the reducing end of the molecule can be linked to different peptides and even the linkage region to the peptides can differ. All this adds up to a large number of possible structural variants. Thus, it seems that some structural variations of GAGs might be specifically related to disease processes and thus serve as candidates as "primary" markers. In any event, the term GAGs as used herein and in the claims which follow, is intended to refer to the above seven classical species and as well, to hybrid forms of these species with or without fragments of protein.

With a concept in mind that one or more of the classical GAGs or their structural variants might be specifically related to disease processes, GAGs may be further investigated as markers of the human prostate. To do so, GAGs may be extracted by papain digestion and partially purified by a routine method. The various species of GAGs may be determined by the usual accepted methods. Although consistent differences among the normal, cancerous and hyperplastic prostates are found, they are nonetheless only gross differences. The usual methods are not designed to point out unique marker GAGs.

Of all of the methods for studying GAGs, the cellulose acetate membrane electrophoresis method seems to offer the best promise in the search for marker GAGs. By using appropriate electrolytes, GAGs can be separated according to their charge densities or backbone structures. Additionally, the separated GAGs can be made altogether visible by staining, for example, with alcian blue.

Referring now to FIG. 1, there is illustrated a group of slides or panels showing electropherograms of GAGs separated in 0.1N HCl. The direction of migration of GAGs is upward from the cathode (at the lower side) toward the anode (at the upper side). The two bands on the left side of panels A and C and the two bands on the right side of panels B and D labeled "G" are two reference GAGs: the faster-moving (upper) band being chondroitin 6-sulfate, and the slower moving (lower) bands being hyaluronate. The other sets or columns of bands labeled C, N and H represent GAGs from cancerous, normal and hyperplastic human prostates, respectively.

Referring specifically to panel B, it can be clearly seen that the GAG patterns of hyperplastic, normal and cancerous prostates are different. These patterns are rather consistent, even though the relative intensity of the bands might differ from specimen to specimen.

Panel A shows the same GAGs after action of the enzyme chondroitinase AC, which is known to specifically depolymerize hyaluronate, chondroitin 6-sulfate, and chondroitin 4-sulfate. Panel D shows the GAGs after action of chondroitinase ABC, the enzyme known to depolymerize dermatan sulfate in addition to those acted on by chondroitinase AC.

Viewing the GAGs in cancer (C), it is evident that the major band was depolymerized by both chondroitinase AC and ABC (panels A and D). However, the action of chondroitinase AC (panel A) produced a broad slow moving band; the action of chondroitinase ABC produced a broad band with an intermediate mobility. These results suggest the presence of GAGs with heterogeneous structures, possibly in the form of copolymers. Inspecting the GAGs of the normal prostate (N), both chondroitinase AC and chondroitinase ABC caused a broadening of the intermediate band with a concomitant relative loss of the slow band. In hyperplasia (H) the very broad and diffused band above the slow moving band is lost by the action of chondroitinase AC as well as of chondroitinase ABC. With a loss of the diffused band, there seems to be a broadening of the slow moving band.

The GAGs of panel C were first digested with chondroitinase ABC in an identical manner as those of panel D. After dialysis, the GAGs in the retentate were treated with nitrous acid, which is known to cleave the sulfamide bond in heparan sulfate. In hyperplasia (H) it appears that nitrous acid had no effect upon the chondroitinase ABC-resistant GAGs. In normal (N), the major band that is resistant to chondroitinase ABC was lost by the action of nitrous acid, but with a broadening of the slow band. In cancer (C), the major chondroitinase ABC-resistant band was somewhat diminished.

The electropherograms of FIG. 1 illustrate the unique GAG patterns of the normal and diseased prostates. They also show the presence of GAGs with heterogeneous structure. However, the presence of disease-specific marker-molecules is not clear. For this reason GAGs may be fractionated by column chromotography using DOWEX 1-X2 (Cl⁻) and eluting with NaCl solutions of various concentrations for further investigation.

Figure 2:
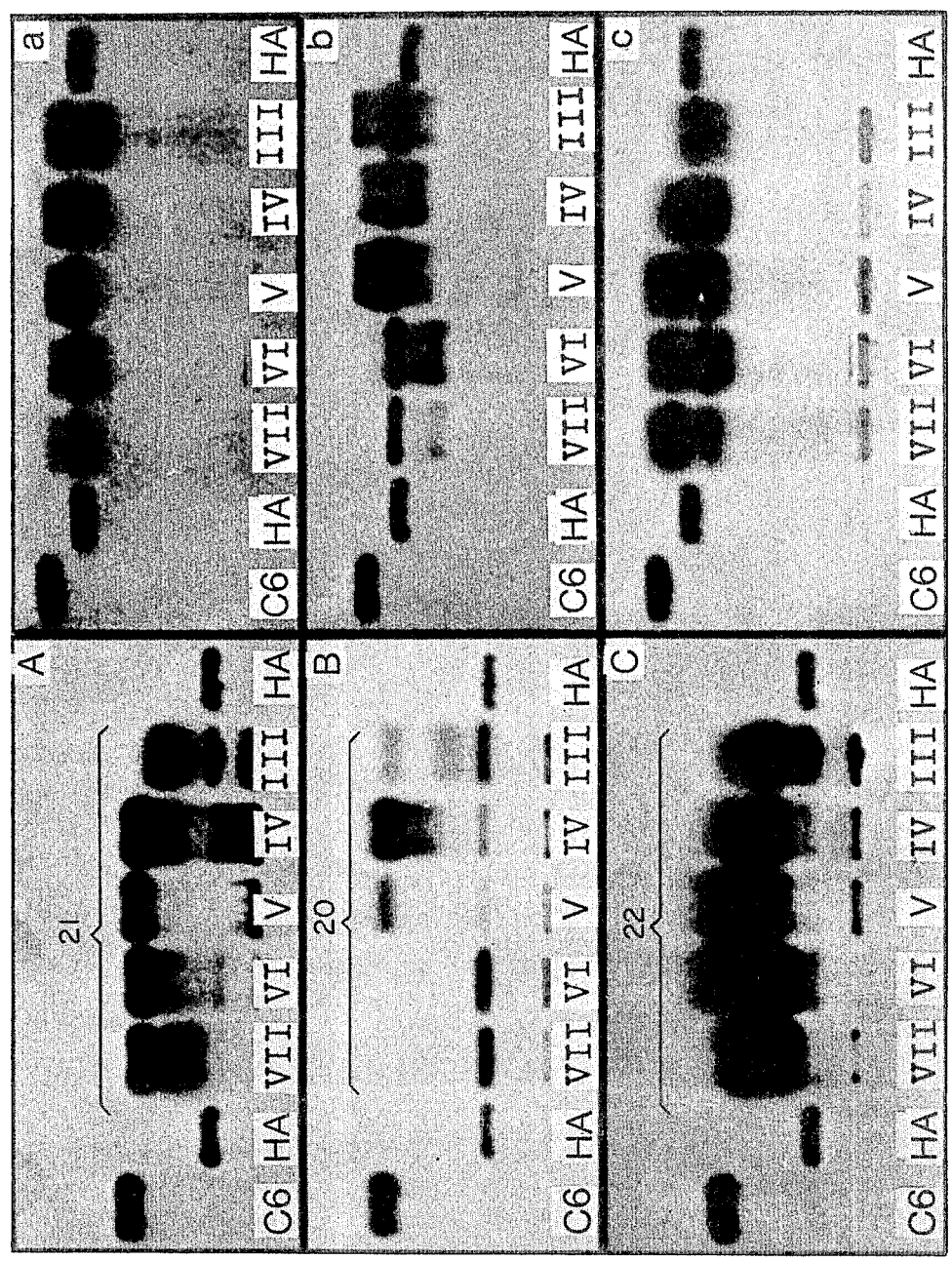
FIG. 2 represents an electropherogram of various fractions of GAGs for normal, cancerous and hyperplastic prostates clearly demonstrating the presence of marker-molecules that are unique to normal, cancerous and hyperplastic human prostates.

The next figure, FIG. 2, illustrates electropherograms of the various fractions. The top row of panels A, a represents GAGs from cancer; the middle row of panels B, b GAGs from normal; and the bottom row of panels C, c represents GAGs from hyperplasia. The index along the bottom of each panel "C6, HA, VII, VI, V, IV, III, HA" indicates reference GAGs chondroitin 6-sulfate, reference GAG hyaluronate, fraction VII, fraction VI, fraction V, fraction IV, fraction III and reference GAG haluronate, respectively.

The GAGs in the left column of panels A, B, C, were separated using 0.1N HCl. This method separates GAGs according to the densities of the negative charges. The higher the charge density, the faster the mobility of the GAGs from cathode (lower) to anode (upper). Once again, the GAG patterns for the three categories appear unique. Normal (panel B) has a band 20 moving like hyaluronate, the GAG reference in column HA. Cancer (panel A) has a band 21 moving like chondroitin 6-sulfate, the GAG reference in column C6. Hyperplasia (panel C) has a broad band 22. The broad band represents varying degrees of sulfation, the most sulfated moving at the front or upper end and the least sulfated moving at the lower or tail end. Thus, it would seem that hyperplasia of the prostate involves a defect in the degradation of the sulfated GAGs or a defect in the regulation or sulfation.

Cancer appears to involve the overproduction of large polymers with a high density of sulfate groups, or the failure to depolymerize them. That the disease processes are much more complicated than suggested is indicated in the electropherograms on the right panels a, b, and c, which were performed the same way as those on the left by using barium acetate instead of 0.1N HCl as the electrolyte. Under this condition, the mobility of the GAGs is highly influenced by their backbone structure.

Comparing the left and right electropherograms of cancer samples (panels A,a) it is clearly evident that the major band in fractions VI and VII moved like chondroitin 6-sulfate in 0.1N HCl (panel A) but moved like hyaluronate in 0.1M barium acetate (panel a). In contrast to the major cancer band, the major normal band fractions VI and VII moved like hyaluronate in both electrolytes as shown by the middle panels B and b. In sharp contrast to the narrow bands present in cancer and in normal samples, the bands in hyperplasia are very broad. In 0.1N HCl (panel C) the bands in fractions VI and VII appear as a single elongated band; however, this band is separated into two rather broad bands in 0.1M barium acetate (panel c).

The results of these tests clearly demonstrate the presence of marker-molecules (GAGs) which are unique to the normal, cancerous and hyperplastic human prostates. Thus, GAGs are proven to be suitable as a disease-specific marker not only for cancer of the prostate but also for hyperplasia. They should prove to be a valuable tool in the diagnosis, prognosis and treatment of cancer and hyperplasia. Using the findings of the present invention, it is expected that antibodies will be found for detecting and observing GAGs by immunoassay.

As previously mentioned, seven classical species of GAGs are recognized. However, it appears that there also exists a large number of structural variants in the form of hybrids or copolymers made up of various lengths of fragments of the species. They may be also linked to fragments of protein. Thus, the term GAGs so used in the specification and claims is intended to cover not only the classical GAG species but the hybrids and copolymers thereof with and without fragments of protein. Furthermore, it is intended that the scope of the invention be limited only by the claims which follow.

I claim:

1. A disease-specific marker for cancer and hyperplasia of the human prostate comprising hybrid and copolymer glycosaminoglycans (GAGs) extracted from the patient.

2. A method of diagnosing cancer and hyperplasia of the human prostate by observing hybrid and copolymer glycosaminoglycans (GAGs) extracted from the patient.

3. A method of monitoring the treatment of cancer and hyperplasia of the human prostate by observing hybrid and copolymer glycosaminoglycans (GAGs) extracted from the patient.

4. A method of diagnosing cancer and hyperplasia of the human prostate as set forth in claim 2 in which said observing of said extracted hybrid and copolymer glycosaminoglycans (GAGs) is accomplished by electrophoresis methods.

5. A method of monitoring the treatment of cancer and hyperplasia of the human prostate as set forth in claim 3 in which said observing of said extracted hybrid and copolymer glycosaminoglycans (GAGs) is accomplished by electrophoresis methods.

* * * * *